(12) United States Patent
Flanagan

(10) Patent No.: US 6,492,615 B1
(45) Date of Patent: Dec. 10, 2002

(54) LASER POLISHING OF MEDICAL DEVICES

(75) Inventor: Aiden Flanagan, Galway (IE)

(73) Assignee: Scimed Life Systems, Inc., Maple Grove, MN (US)

(*) Notice: Subject to any disclaimer, the term of this patent is extended or adjusted under 35 U.S.C. 154(b) by 27 days.

(21) Appl. No.: 09/689,142

(22) Filed: Oct. 12, 2000

(51) Int. Cl.⁷ .................. B23K 26/00; B23K 26/08
(52) U.S. Cl. .................. 219/121.66; 219/121.8
(58) Field of Search .............. 219/121.6, 121.61, 219/121.62, 121.64, 121.65, 121.66, 121.85, 121.86, 92, 121.8; 427/554–556

(56) References Cited

U.S. PATENT DOCUMENTS

| | | | |
|---|---|---|---|
| 4,661,676 A | * 4/1987 | Morita et al. | 148/903 |
| 4,731,516 A | * 3/1988 | Noguchi et al. | 117/50 |
| 4,832,798 A | * 5/1989 | Cvijanovich et al. | 205/209 |
| 5,068,514 A | 11/1991 | Lunney | 219/121.69 |
| 5,178,158 A | 1/1993 | de Toledo | 128/772 |
| 5,203,777 A | 4/1993 | Lee | 604/280 |
| 5,226,101 A | 7/1993 | Szentesi et al. | 385/85 |
| 5,246,530 A | 9/1993 | Bugle et al. | 156/643 |
| 5,344,425 A | 9/1994 | Sawyer | 606/198 |
| 5,370,691 A | 12/1994 | Samson | 623/12 |
| 5,385,152 A | 1/1995 | Abele et al. | 128/772 |
| 5,421,955 A | * 6/1995 | Lau et al. | 216/48 |
| 5,549,552 A | 8/1996 | Peters et al. | 604/96 |
| 5,556,413 A | 9/1996 | Lam | 606/198 |
| 5,607,444 A | 3/1997 | Lam | 606/194 |
| 5,628,787 A | 5/1997 | Mayer | 623/1 |
| 5,630,840 A | 5/1997 | Mayer | 623/1 |
| 5,632,771 A | 5/1997 | Boatman et al. | 623/1 |
| 5,639,278 A | 6/1997 | Dereume et al. | 623/1 |
| 5,656,186 A | 8/1997 | Mourou et al. | 219/121.69 |
| 5,679,470 A | 10/1997 | Mayer | 428/662 |
| 5,718,724 A | 2/1998 | Goicoechea et al. | 623/1 |
| 5,725,549 A | 3/1998 | Lam | 606/198 |

(List continued on next page.)

FOREIGN PATENT DOCUMENTS

| | | |
|---|---|---|
| EP | 0 366 355 | 5/1990 |
| EP | 0 778 011 | 6/1997 |
| WO | 97/33534 | 9/1997 |

OTHER PUBLICATIONS

U.S. Patent Application Ser. No. 09/458851, Flanagan, filed Dec. 10, 1990.
U.S. Patent Application Ser. No. 09/654987, Flanagan, filed Sep. 5, 2000.

(List continued on next page.)

*Primary Examiner*—Tom Dunn
*Assistant Examiner*—Zidia Pittman
(74) *Attorney, Agent, or Firm*—Vidas, Arrett & Steinkraus

(57) ABSTRACT

A desired portion of a stent may be polished by irradiating at least a portion of the surface of the stent substrate with a laser beam from the laser at a wavelength absorbed by the stent substrate to cause a controlled level of melting of the surface of the stent substrate and allowing the substrate material to solidify.

36 Claims, 3 Drawing Sheets

U.S. PATENT DOCUMENTS

| | | | |
|---|---|---|---|
| 5,725,570 A | 3/1998 | Heath | 623/1 |
| 5,725,572 A | 3/1998 | Lam et al. | 623/1 |
| 5,733,301 A * | 3/1998 | Forman | 604/96.01 |
| 5,733,326 A | 3/1998 | Tomonto et al. | 623/1 |
| 5,741,327 A | 4/1998 | Frantzen | 623/1 |
| 5,746,691 A | 5/1998 | Frantzen | 600/36 |
| 5,780,807 A * | 7/1998 | Saunders | 219/121.71 |
| 5,788,558 A | 8/1998 | Klein | 451/36 |
| 5,800,511 A | 9/1998 | Mayer | 623/1 |
| 5,824,042 A | 10/1998 | Lombardi et al. | 623/1 |
| 5,824,045 A | 10/1998 | Alt | 623/1 |
| 5,824,077 A | 10/1998 | Mayer | 623/11 |
| 5,836,964 A | 11/1998 | Richter et al. | 606/194 |
| 5,836,969 A | 11/1998 | Kim et al. | 606/200 |
| 5,852,277 A * | 12/1998 | Gustafson | 219/121.67 |
| 5,855,802 A | 1/1999 | Acciai et al. | 216/8 |
| 5,858,556 A | 1/1999 | Eckert et al. | 428/586 |
| 5,868,777 A | 2/1999 | Lam | 606/194 |
| 5,902,475 A | 5/1999 | Trozera et al. | 205/655 |
| 5,916,263 A | 6/1999 | Goicoechea et al. | 623/1 |
| 5,925,069 A * | 7/1999 | Graves et al. | 607/36 |
| 5,938,696 A | 8/1999 | Goicoechea et al. | 623/1 |
| 5,968,068 A | 10/1999 | Dehdashtian et al. | 606/192 |
| 5,980,553 A | 11/1999 | Gray et al. | 606/198 |
| 6,004,279 A | 12/1999 | Crowley et al. | 600/585 |
| 6,004,328 A | 12/1999 | Solar | 606/108 |
| 6,004,347 A | 12/1999 | McNamara et al. | 623/1 |
| 6,013,854 A * | 1/2000 | Moriuchi | 606/194 |
| 6,022,374 A | 2/2000 | Imran | 623/1 |
| 6,023,040 A * | 2/2000 | Zahavi et al. | 219/121.69 |
| 6,027,528 A | 2/2000 | Tomonto et al. | 623/1 |
| 6,043,452 A * | 3/2000 | Bestenlehrer | 219/121.62 |
| 6,086,455 A | 7/2000 | Frantzen | 451/36 |
| 6,099,561 A | 8/2000 | Alt | 623/1.44 |
| 6,110,191 A | 8/2000 | Dehdashtian et al. | 606/192 |
| 6,342,067 B1 * | 1/2002 | Mathis et al. | 623/1.15 |

* cited by examiner

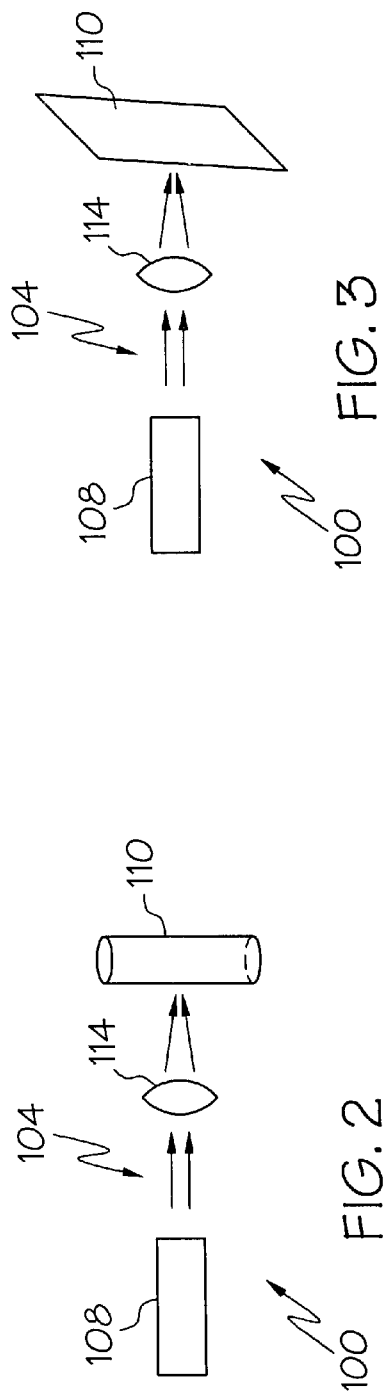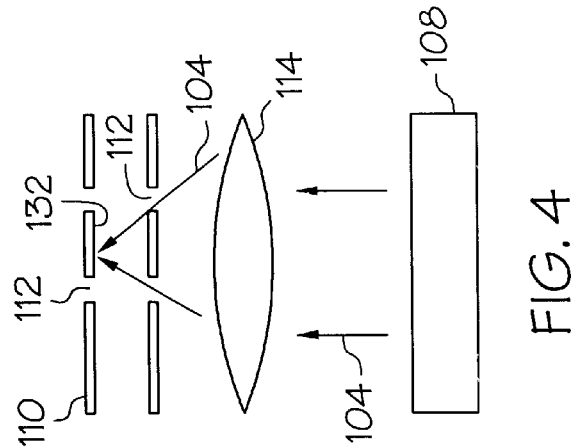

LASER POLISHING OF MEDICAL DEVICES

BACKGROUND OF THE INVENTION

Prior to insertion of a stent in a bodily vessel, it is typically necessary to polish the stent to eliminate sharp corners on the edges of the stent and to provide as smooth a surface as possible. The presence of sharp edges may directly damage a vessel and may provide a site for collection of plaque and other deposits. Where the stent is balloon expandable, the presence of sharp edges may also lead to balloon bursts. A rough stent surface may result in medical complications such as the formation of thrombi and restenosis.

Other implantable medical devices for which polishing may be beneficial include vena cava filters.

A number of techniques have been used to polish stents and vena cava filters. One such technique involves the use of an abrasive to polish the material from which the stent is formed. Where polishing is not possible prior to stent formation, the formed stent may be polished using abrasives or electropolishing techniques. The use of abrasives to polish a stent is disclosed in U.S. Pat. No. 5,746,691, U.S. Pat. No. 5,788,558, U.S. Pat. No. 5,902,475 and U.S. Pat. No. 6,086,455. An electropolishing technique is disclosed in U.S. Pat. No. 5,344,425. Electropolishing techniques typically polish surfaces to a mean roughness $R_a$ of 300–400 nm. Electropolishing is only suitable on certain surfaces, however, such as stainless steel, copper alloys and aluminum alloys.

Electrpolishing has also been used to polish medical guidewires as disclosed in U.S. Pat. No. 5,178,158.

There remains a need for novel techniques for polishing stents, vena cava filters and medical guidewires which result in smoother surfaces.

All U.S. patents and applications and all other published documents mentioned anywhere in this application are incorporated herein by reference in their entirety.

The invention in various of its embodiment is summarized below. Additional details of the invention and/or additional embodiments of the invention may be found in the Detailed Description of the Invention below.

BRIEF SUMMARY OF THE INVENTION

In one embodiment, the invention is directed to a method of polishing at least a portion of a stent substrate. The method comprises the steps of providing a stent substrate, providing a laser operating at a wavelength absorbable by the stent substrate and irradiating the surface of the stent substrate with a laser beam from the laser at a wavelength absorbed by the stent substrate to cause a controlled level of melting of the surface of the stent substrate. Finally, the stent substrate is allowed to solidify.

The invention is also directed to a method of polishing at least a portion of a stent substrate comprising the steps of providing a stent substrate, providing a laser operating at a wavelength absorbable by the stent substrate and directing a laser beam output from the laser at a portion of the stent substrate, the laser beam characterized by a fluence of between about 1 J/cm$^2$ and 5000 J/cm$^2$.

The invention is also directed to a method of polishing at least a portion of a stent substrate comprising the steps of providing a stent substrate, providing a laser operating at a wavelength absorbable by the stent substrate and directing a laser beam output from the laser at a portion of the stent substrate, the laser beam melting a surface layer of the stent substrate to a depth of no greater than 5 percent of the thickness of the stent substrate in the portion of the stent substrate impinged by the laser beam.

The invention is further directed to a method of polishing at least a portion of a medical guidewire for use with a catheter. The method comprises the steps of providing a medical guidewire, providing a laser and irradiating the surface of the guidewire with a beam of radiation from the laser at a wavelength absorbed by the guidewire to cause a controlled level of melting of the surface of the guidewire in the portion of the guidewire impinged by the laser beam. Finally, the surface of the guidewire is allowed to solidify.

The invention is also directed to a method of polishing at least a portion of a guidewire comprising the steps of providing a guidewire, providing a laser operating at a wavelength absorbable by the guidewire and directing a laser beam output from the laser at a portion of the guidewire, the laser beam melting a surface layer of the guidewire to a depth of no greater than 5 percent of the thickness of the guidewire in the portion of the guidewire impinged by the laser beam.

The invention is also directed to a method of polishing at least a portion of a component for use with a catheter system. The method comprises the steps of providing the component for use with a catheter system, providing a laser operating at a wavelength absorbable by the component for use with a catheter system and directing a laser beam output from the laser at a portion of the component for use with a catheter system, the laser beam melting a surface layer of the component for use with catheter system to a depth of no greater than 5 percent of the thickness of the component in the portion of the component impinged by the laser beam.

BRIEF DESCRIPTION OF THE SEVERAL VIEWS OF THE DRAWING(S.

FIG. 2 is a schematic illustration of polishing a tubular stent substrate using a laser;

FIG. 3 is a schematic illustration of polishing a stent substrate in the form of a sheet using a laser;

FIG. 4 is a schematic illustration of polishing the inner surface of a tubular stent substrate using a laser;

DETAILED DESCRIPTION OF THE INVENTION

Figure 1:
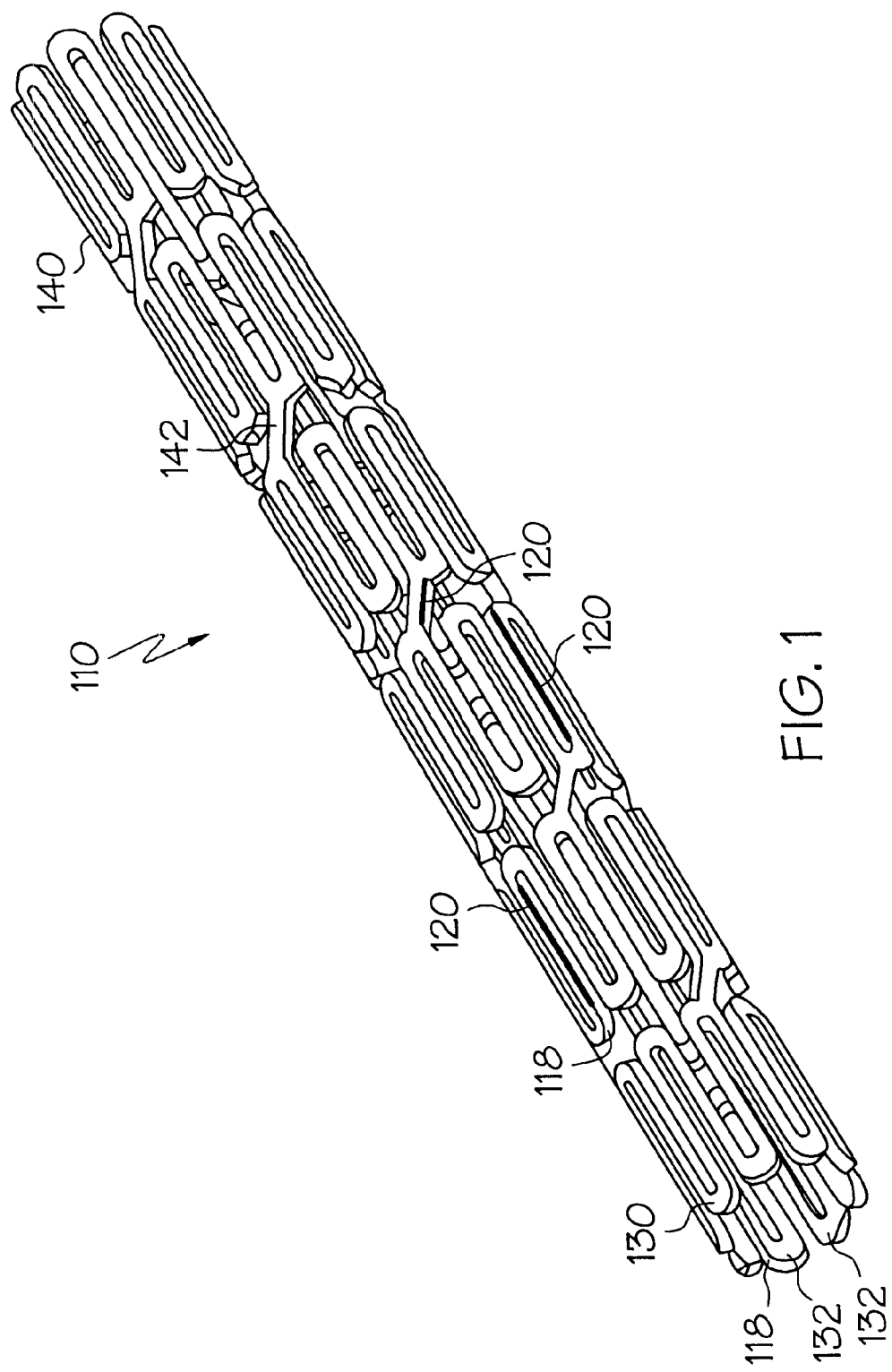
FIG. 1 is a side elevational view of a tubular stent substrate.

While this invention may be embodied in many different forms, there are described in detail herein specific preferred embodiments of the invention. This description is an exemplification of the principles of the invention and is not intended to limit the invention to the particular embodiments illustrated.

For the purpose of this disclosure, unless otherwise indicated, identical reference numerals used in different figures refer to the same component.

Also for the purpose of this disclosure, the term "stent substrate" refers to stents as well as stent precursors. Stent precursors include sheets of material prior to being rolled or otherwise formed into tubular stents. The sheets may have stent patterns cut or otherwise formed therein. Stent precursors also included tubes with or without stent patterns cut or otherwise formed therein.

An exemplary tubular stent substrate is shown at 110 in FIG. 1. Stent substrate 110 has an outer surface 130, an inner surface 132 and side surfaces 118 extending between outer surface 130 and inner surface 132. Edges 120 are formed by the intersections between the inner surfaces and the side surfaces and by the intersections between the outer surfaces and the side surfaces. Stent 110 comprises a plurality of interconnected serpentine bands 140. Each band 140 comprises a plurality of interconnected struts 142. Adjacent bands are joined together by connecting members 144.

An arrangement for carrying the inventive smoothing methods is shown generally at 100 in FIG. 2. Laser beam 104 output from laser 108 is directed toward the surface of stent substrate 110. Laser 104 is a pulsed Nd:YAG laser operating at a wavelength of 1.064 μm. Any other suitable laser which outputs radiation which can melt a surface layer of the stent substrate may also be used. The specific choice of laser will depend on the material on the surface of the stent substrate. For example, when the surface of the stent substrate is made from polymeric material, an excimer laser or a $CO_2$ laser may be used. Where the surface of the stent substrate is made from metal, such as stainless steel or nitinol, a Nd:YAG laser, $CO_2$ laser, frequency doubled YAG laser, diode laser or other laser may be used. Where the stent is coated with gold, a pulsed Nd:YAG laser operating at the 532-nm, second-harmonic wavelength may be used. Other facets of laser processing of stents with gold have been disclosed in copending U.S. application Ser. No. 09/458,851 now pending. Laser beam 108 is focused to a spot using optical element 114. Optical element 114 may comprise a single lens as shown in FIG. 2 or a plurality of lenses for focusing the beam to a desired spot size. The stent substrate surface in the region of the beam and a thin underlayer melts and is allowed to solidify, thereby polishing the stent substrate.

Without being bound by theory, it is believed that the polishing effect is achieved by molten liquid surface tension and gravity which smooths out the liquid metal before solidification.

The depth of the melt region is controlled primarily by the amount of energy delivered to the irradiated area and the dwell time, i.e. the period during which a particular location on the substrate surface is irradiated. In the case of a pulsed laser beam, the dwell time is controlled by the pulse duration and pulse frequency. The amount of energy is controlled by the power at which the beam is generated, by any attenuation between the beam source and area of impingement, by the degree of beam focusing and by the spatial characteristics of the beam.

By adjusting the amount of energy delivered to the irradiated area and the dwell time, it is possible to melt and polish a thin surface layer of material without significantly raising the temperature of the underlying layers of the stent substrate thereby avoiding changing any temperature dependent properties of the underlying layers of the stent substrate. Where the stent substrate material has a low heat conductance and a high heat capacity, longer pulse durations may be used. Where the material has a high heat conductance and a low heat capacity, shorter pulse durations should be used. A mean surface roughness $R_a$ as low as 20 nm or less may be achieved using the inventive methods. Waves in the surface of the stent substrate may also be smoothed out using the inventive methods.

Desirably, a pulsed laser will be used. If a continuous laser is used, the laser beam may be modulated by shutter, for example, mechanical or optical to avoid excessive energy deposition. Excessive energy deposition may also be avoided by moving one of the stent substrate or the laser beam relative to the other.

The stent substrate may be tubular as shown in FIG. 2 or in the form of a sheet as shown in FIG. 3. Where the stent substrate is in sheet form during polishing, both sides of the sheet may be polished so that both the inner surface and the outer surface of the resulting stent will be polished. Because the technique is a line of sight technique, treating both sides of a sheet prior to forming a tube allows for a simpler polishing process than is possible with a stent formed from a tube.

In the case of a tubular stent substrate, as shown in FIG. 4, the inner surface 132 of the stent substrate 110 may be polished by directing and focusing laser beam 104 through the gaps 112 between adjacent struts using optical element 114. Stent substrate 110 is shown in longitudinal cross-section. By selecting a small depth of field of the focused laser beam, the outer surface of the stent may remain unaffected by the laser beam because of the lower intensity of the beam in that region while the inner surface is polished.

The invention contemplates polishing selected portions of the stent substrate or the entirety of the stent substrate. The exterior surface of the stent may be polished by impinging laser beam 108 at an angle normal to the exterior surface of stent substrate 110 as shown with tubular stent substrate in FIG. 2 and a sheet stent substrate in FIG. 3.

Figure 5:
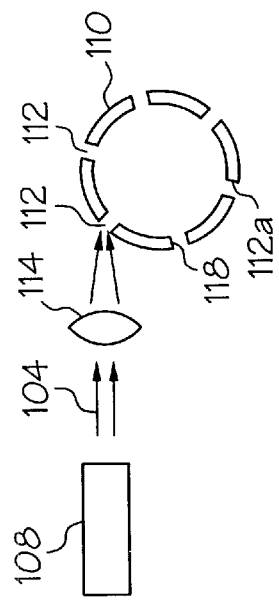
FIG. 5 is a schematic illustration of polishing the outer surface of a tubular stent substrate using a laser.

As shown in FIG. 5, the outer diameter of a tubular stent substrate may also be polished by focusing a laser beam 104 via optical element 114 such that the required laser intensity occurs at the outer surface 130 of stent substrate 110. Any part of the beam that penetrates through gaps 112 between struts is designed to be diverging so that a lower intensity beam illuminates the inner surface 132 of the tubular stent substrate and has no polishing effect. Stent substrate 110 is shown in transverse cross-section in FIG. 5.

Figure 7:
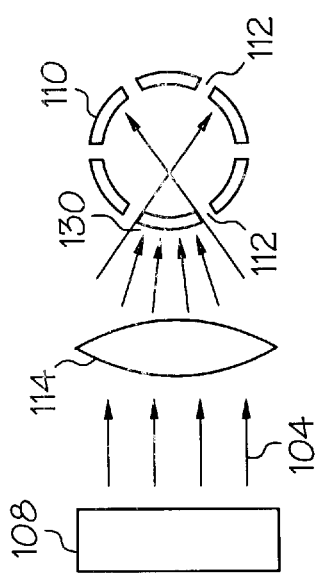
FIG. 7 is a schematic illustration of polishing the edges of a stent substrate in the form of a sheet using a laser.
Figure 6:
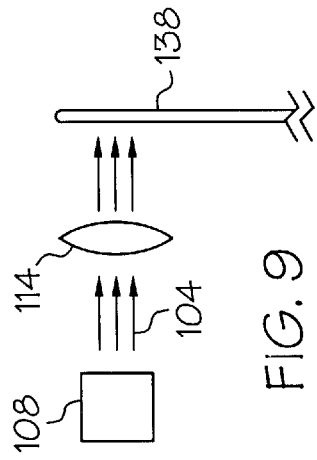
FIG. 6 is a schematic illustration of polishing the edges of the struts of a tubular stent substrate using a laser.

The edges or side surfaces of the struts of the stent may be polished by directing a tangential beam 104 toward tubular stent substrate 110 as shown in FIG. 6 and sheet stent substrate in FIG. 7. Tangential beam 104 impinges side surfaces 118 and edges 120 of stent substrate 110 thereby polishing side surface 118 and edge 120 of the stent substrate. Stent substrate 110 is shown in transverse cross-section in FIG. 6 and in longitudinal cross-section in FIG. 7.

Selected portions of the stent substrate may also be polished by masking portions of the stent substrate. The mask may comprise a coating of an appropriate maskant on the surface of the stent substrate or the mask may comprise a separate device which is disposed at least partially in the path of the beam.

In treating the stent substrate, the laser may be held stationary and the stent substrate rotated and/or translated or otherwise moved in the path of the beam. Alternatively, the stent substrate may be held stationary by any suitable device including a mandril and the laser beam moved. In the latter case, the beam may be moved by moving the laser itself or by refocusing the beam via the optical system. For example, in the case of a tubular stent substrate, the laser may be mounted on a ring disposed about the stent substrate and moved along the ring about the circumference of the stent substrate. The ring may also be translated in a longitudinal direction relative to the stent substrate or the ring may be fixed in place and the stent substrate moved in a longitudinal direction. The beam may also be focused into a ring as disclosed in commonly assigned and cofiled U.S. patent application Ser. No. 09/654,987 now pending entitled Method of Applying a Laser Beam Around the Circumference of a Catheter now pending, so as to polish a circumferential band.

Where the stent substrate is in the form of a tube, a stent pattern may be cut therein desirably prior to laser polishing. The invention also contemplates cutting the stent pattern in the tube subsequent to laser polishing.

Similarly, where the stent substrate is in the form of a sheet, a stent pattern may desirably be cut into the sheet prior to polishing. The invention also contemplates cutting the pattern into the sheet subsequent to polishing. Regardless of when the polishing is done, the sheet is then rolled into a tube and welded. The welded stent may then be subjected to additional polishing, whether laser polishing, electropolishing or abrasive polishing along the weld to remove any surface irregularities resulting from the weld.

Techniques for cutting stent patterns in tubes and sheets are well known in the art and include laser etching, chemical etching, mechanical cutting and electrodischarge machining.

In the practice of the invention, where a stent substrate containing a readily oxidizable metal, for example, stainless steel or titanium, is being polished, it may be desirable to exclude oxygen from the substrate surface. This may be accomplished by providing an inert shield gas about the stent substrate. For example, the stent substrate may be placed in a chamber and an inert gas provided in the chamber. Suitable inert gases include nitrogen, argon, krypton, xenon and any other gases that prevent oxidation. Oxygen may also be excluded by providing the stent substrate in a chamber and evacuating the chamber. Desirably, the chamber will be evacuated prior to irradiating the stent substrate and the chamber maintained under vacuum during the irradiation. Irradiating under a vacuum also reduces the likelihood of plasma formation. Oxygen removal is not an issue where the stent substrate material is not readily oxidized such as gold.

In accordance with the invention, a stainless steel stent substrate may be polished using a pulsed Nd:Yag laser operating at 1.064 $\mu$m. The laser energy may be delivered directed or via a fiber. A single pulse of duration ranging from 10 $\mu$s to 1 ms with a pulse energy ranging from 1 mJ to 1 J and a spot size of about 100 $\mu$m to about 800 $\mu$m in diameter is sufficient to polish the portion of the stent irradiated by the beam. Desirably, the pulse duration will range from 10 $\mu$s to 0.1 ms and will be focused to a spot size of 400 $\mu$m with a depth of focus of 0.5 mm using a lens with a 100 mm focal length. Also desirably, the pulse energy will range from 50 mJ to 250 mJ. Where portions of the stent in excess of the spot size are to be polished, the pulse repetition rate is from about 1 Hz to about 50 Hz. Desirably a pulse repetition of about 1 Hz is used for polishing regions exceeding the spot size. It is noted that these parameters are exemplary. Parameters outside of the above ranges may also be used to polish a stent. For example, where the beam is focused to a smaller spot size, a pulse of shorter duration and/or lower energy may be used. The parameters are selected to allow for sufficient surface melting for polishing without excessive melting.

The invention is also directed to a method of polishing at least a portion of a stent substrate comprising the steps of providing a stent substrate, providing a laser operating at a wavelength absorbable by the stent substrate and directing a laser beam output from the laser at a portion of the stent substrate, the laser beam characterized by a fluence of between about 1 J/cm$^2$ and 5000 J/cm$^2$. Within this range, the surface of the stent substrate is rendered smooth and polished.

The invention is also directed to a method of polishing at least a portion of a stent substrate comprising the steps of providing a stent substrate, providing a laser operating at a wavelength absorbable by the stent substrate and directing a laser beam output from the laser at a portion of the stent substrate, the laser beam melting a surface layer of the stent substrate to a depth of no greater than 5 percent of the thickness of the stent substrate in the portion of the stent substrate impinged by the laser beam. As discussed above, the depth of the melting may be controlled by the amount of power delivered to the surface of the stent substrate. If an excessive amount of power is delivered to the stent substrate and the stent substrate is melted to a depth in excess of 5 percent of the thickness of the stent substrate, the physical properties of the stent may be undesirably altered.

The invention also contemplates laser polishing a stent substrate in combination with other polishing techniques. For example, laser polishing may precede or follow electropolishing of a stent substrate or abrasive polishing of a stent substrate. Moreover, certain regions of a stent substrate may be polished via electropolishing or abrasive polishing and other regions of the stent may be polished using laser polishing.

It is noted that a laser beam, generated at power levels comparable to those used in laser polishing but focused to a substantially smaller irradiation area, has been found to form a dimple or a depression on the substrate surface. The formation of dimples or depressions is believed to be due to the Gaussian shaped intensity profile of the laser beam. It may be desirable to form such dimples or depressions over desired portions of the stent to prevent slippage between a stent and a balloon.

The inventive methods may be used to polish a variety of stent substrates including polymeric stent substrates and metal stent substrates and stent substrates made from a combination of polymeric and metallic materials. In the case of metal stent substrates, the inventive techniques may be used to polish stent substrates made from a single metal or stent substrates made from a plurality of metals, including plated or otherwise coated stent substrates. Such stent substrate include stent substrates formed of a base metal such as stainless steel and coated with a precious metal such as gold are known in the art. The inventive methods have proven particularly useful in polishing gold plated stainless steel stent substrates.

Figure 8:
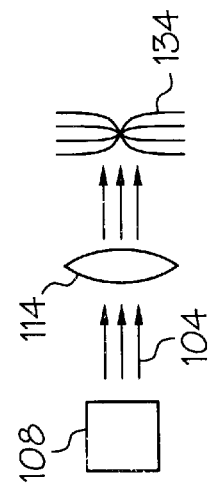
FIG. 8 is a schematic illustration of polishing a vena cava filter.

The inventive methods may also be used to polish a variety of other medical devices which are designed to be implantable in bodily lumen including vena cava filters. An example of a vena cava filter is shown in U.S. Pat. No. 5,836,969. Vena cava filters may be polished using any of the techniques discussed above with respect to stent substrates. As shown in FIG. 8, laser beam 104 generated by laser 108 is focused by lens 114 and directed at vena cava filter 134 to polish the vena cava filter.

Figure 9:
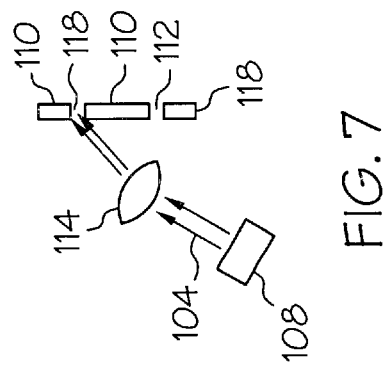
FIG. 9 is a schematic illustration of polishing a medical guidewire.

The inventive methods may also be used to polish medical guidewires. An example of a guidewire is disclosed in U.S. Pat. No. 6,004,279 and U.S. Pat. No. 5,385,152. As shown in FIG. 9, laser beam 104 generated by laser 108 is focused by lens 114 and directed at guidewire 138 to polish the guidewire.

To that end, the invention is further directed to a method of polishing at least a portion of a medical guidewire for use with a catheter. The method comprises the steps of providing a medical guidewire, providing a laser; and irradiating the surface of the guidewire with a beam of radiation from the laser at a wavelength absorbed by the guidewire to cause a controlled level of melting of the surface of the guidewire. Finally, the surface of the guidewire is allowed to solidify.

The invention is also directed to a method of polishing at least a portion of a guidewire comprising the steps of providing a guidewire, providing a laser operating at a wavelength absorbable by the guidewire and directing a laser beam output from the laser at a portion of the guidewire, the laser beam melting a surface layer of the guidewire to a depth of no greater than 5 percent of the thickness of the guidewire in the portion of the guidewire impinged by the laser beam.

Select portions of the medical guidewire may be polished or the entirety of the medical guidewire may be polished using the inventive methods. The guidewire may be rotated and/or translated relative to the laser beam or the laser beam may be moved relative to the guidewire.

The invention is also directed to a method of polishing at least a portion of a component for use with a catheter system. The method comprises the steps of providing the component for use with a catheter system, providing a laser operating at a wavelength absorbable by the component for use with a catheter system and directing a laser beam output from the laser at a portion of the component for use with a catheter system, the laser beam melting a surface layer of the component for use with catheter system to a depth of no greater than 5 percent of the thickness of the component in the portion of the component impinged by the laser beam. The component may be a stent, a vena cava filter or a guidewire.

Any of the above-mentioned inventive methods may be combined with conventional polishing techniques.

In addition to being directed to the embodiments described above and claimed below, the present invention is further directed to embodiments having different combinations of the dependent features described above and claimed below.

The above disclosure is intended to be illustrative and not exhaustive. This description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A method of polishing at least a portion of a stent substrate comprising the steps of:
   providing a stent substrate;
   providing a laser operating at a wavelength absorbable by the stent substrate; and
   irradiating at least a portion of the surface of the stent substrate with a laser beam from the laser at a wavelength absorbed by the stent substrate to cause a controlled level of melting of the surface of the stent substrate; and
   allowing the substrate material to solidify.

2. The method of claim 1 further comprising the step of providing an inert gas about the stent during the irradiating step.

3. The method of claim 2 wherein the surface of the stent substrate comprises stainless steel.

4. The method of claim 1 wherein the stent substrate is placed in a chamber prior to the irradiating step and the chamber evacuated prior to the irradiating step.

5. The method of claim 4 wherein the stent substrate is maintained in a vacuum during the irradiating step.

6. The method of claim 5 wherein the surface of the stent substrate comprises stainless steel.

7. The method of claim 1 wherein the entirety of the stent substrate is polished.

8. The method of claim 7 wherein the laser is scanned across a portion of the stent substrate.

9. The method of claim 1 wherein the laser is pulsed.

10. The method of claim 1 wherein the laser is a continuous laser and the laser beam is modulated.

11. The method of claim 10 wherein the laser beam is modulated by a shutter.

12. The method of claim 11 wherein the shutter is mechanical or optical.

13. The method of claim 1 wherein the stent substrate is made of polymeric material.

14. The method of claim 13 wherein the laser is an excimer laser or a $CO_2$ laser.

15. The method of claim 1 wherein the stent substrate is made of metal.

16. The method of claim 1 wherein the stent comprises a coating.

17. The method of claim 16 wherein the coating is gold.

18. The method of claim 1 further comprising the step of electropolishing at least a portion of the stent substrate.

19. The method of claim 1 wherein the stent substrate is a sheet, the method further comprising the steps of rolling the sheet and welding the sheet to form a tube.

20. The method of claim 19 wherein the sheet has pattern cut therein via a method selected from the group consisting of laser etching, chemical etching, mechanical cutting and electrodischarge machining.

21. The method of claim 1 wherein the stent substrate is a tube.

22. The method of claim 21 wherein the tube has a pattern cut therein via a method selected from the group consisting of laser etching, chemical etching, mechanical cutting and electrodischarge machining.

23. The method of claim 1 wherein the stent substrate has an inner surface and an outer surface and the laser beam is directed at a portion of the inner surface of the stent to polish the portion of the inner surface of the stent.

24. The method of claim 1, the stent substrate having an inner surface, an outer surface and a plurality of side surfaces extending between the inner surface and the outer surface, wherein the laser beam is directed at a portion of at least one of the side surfaces of the stent to polish the portion of the side surface.

25. The method of claim 24 wherein all of the side surfaces are polished.

26. The method of claim 1, the stent substrate having an inner surface, an outer surface a plurality of side surfaces extending between the inner surface and the outer surface and a plurality of edges, the edges formed at the intersections of the inner surface and the side surfaces and at the intersections of the outer surface and the side surfaces wherein the laser beam is directed at a portion of at least one edge to polish the portion of the edge.

27. The method of claim 26 wherein all of the edges are polished.

28. A method of polishing at least a portion of a stent substrate comprising the steps of:

providing a stent substrate;

providing a laser operating at a wavelength absorbable by the stent substrate;

directing a laser beam output from the laser at a portion of the stent substrate, the laser beam characterized by a fluence of between about 1 J/cm$^2$ and 5000 J/cm$^2$, wherein the wavelength of the laser beam absorbed by the stent substate causes a controlled level of melting of the surface of the stent substrate.

29. The method of claim 28 wherein the laser is pulsed.

30. The method of claim 28 wherein the laser beam is characterized by an intensity of between $10^4$ and $10^6$ Watts/cm$^2$.

31. A method of polishing at least a portion of a stent substrate comprising the steps of:

providing a stent substrate;

providing a laser operating at a wavelength absorbable by the stent substrate;

directing a laser beam output from the laser at a portion of the stent substrate, the laser beam melting a surface layer of the stent substrate to a depth of no greater than 5 percent of the thickness of the stent substrate in the portion of the stent substrate impinged by the laser beam.

32. A method of polishing at least a portion of a medical guidewire for use with a catheter comprising the steps of:

providing a medical guidewire;

providing a laser; and irradiating the surface of the guidewire with a beam of radiation from the laser at a wavelength absorbed by the guidewire to cause a controlled level of melting of the surface of the guidewire in the portion of the guidewire impinged by the laser beam; and allowing the surface of the guidewire to solidify.

33. A method of polishing at least a portion of a guidewire comprising the steps of:

providing a guidewire;

providing a laser operating at a wavelength absorbable by the guidewire;

directing a laser beam output from the laser at a portion of the guidewire, the laser beam melting a surface layer of the guidewire to a depth of no greater than 5 percent of the thickness of the guidewire in the portion of the guidewire impinged by the laser beam.

34. A method of polishing at least a portion of a component for use with a catheter system comprising the steps of:

providing the component for use with a catheter system;

providing a laser operating at a wavelength absorbable by the component for use with a catheter system;

directing a laser beam output from the laser at a portion of the component for use with a catheter system, the laser beam melting a surface layer of the component for use with catheter system to a depth of no greater than 5 percent of the thickness of the component in the portion of the component impinged by the laser beam.

35. The method of claim 34 wherein the component is a stent or vena cava filter.

36. The method of claim 34 wherein the component is a guidewire.

* * * * *